United States Patent [19]

Haaland et al.

[11] Patent Number: 6,066,458
[45] Date of Patent: May 23, 2000

[54] METHODS, APPARATUS AND COMPUTER PROGRAM PRODUCTS FOR DETERMINING QUANTITIES OF NUCLEIC ACID SEQUENCES IN SAMPLES USING STANDARD CURVES AND AMPLIFICATION RATIO ESTIMATES

[75] Inventors: Perry D. Haaland; James G. Nadeau, both of Chapel Hill; Colleen M. Nycz; Cheryl H. Dean, both of Raleigh; Catherine A. Spargo, Apex, all of N.C.

[73] Assignee: Becton, Dickinson and Company, Franklin Lakes, N.J.

[21] Appl. No.: 09/080,589

[22] Filed: May 18, 1998

[51] Int. Cl.⁷ ............................................. C12Q 1/68
[52] U.S. Cl. ........................... 435/6; 435/91.1; 435/91.2; 435/91.21; 435/91.51; 536/221; 536/231; 536/24.3; 536/25.32; 536/23.7; 935/77
[58] Field of Search ...................... 435/6, 91.2, 91.21, 435/91.51, 91.1; 536/221, 231, 24.3, 25.32, 23.7; 935/77

[56] References Cited

U.S. PATENT DOCUMENTS

| | | | |
|---|---|---|---|
| 5,270,184 | 12/1993 | Walker et al. | 435/91.2 |
| 5,455,166 | 10/1995 | Walker | 435/91.2 |
| 5,457,027 | 10/1995 | Nadeau et al. | 435/6 |
| 5,547,861 | 8/1996 | Nadeau et al. | 435/91.2 |
| 5,550,025 | 8/1996 | Walker | 435/6 |
| 5,593,867 | 1/1997 | Walker et al. | 435/91.2 |
| 5,710,029 | 1/1998 | Ryder et al. | 435/911 |
| 5,736,333 | 4/1998 | Livak et al. | 435/6 |
| 5,863,736 | 1/1999 | Haaland et al. | 435/6 |

FOREIGN PATENT DOCUMENTS

| | | | |
|---|---|---|---|
| 0 512 334 A2 | 11/1992 | European Pat. Off. | C12Q 1/68 |
| 0 640 828 A1 | 3/1995 | European Pat. Off. | G01N 21/64 |
| 0 686 699 A2 | 12/1995 | European Pat. Off. | C12Q 1/68 |
| WO95/30139 | 11/1995 | WIPO | G01N 21/64 |

OTHER PUBLICATIONS

Gibson et al.; "A Method for Real Time Quantitative RT–PCR"; *Genome Research*, 6:995–1001 (1996).

Heid et al.; "Real Time Quantitative PCR"; *Genome Research*, 6:986–994 (1996).

A. Rashtchian; "Amplification of RNA"; *PCR Methods and Applications*, 4:S83–S91 (1994).

Rodriquez et al.; "A Novel Method for the Isolation of Tissue–Specific Genes"; *Nucleic Acids Res.*, 20(13):3528 (1992).

Edmands et al.; "Rapid RT–PCR Amplification from Limited Cell Numbers"; *PCR Methods and Applications*, 3:17–319 (1994).

McCulloch et al.; "An Evaluation of Competitor Type and Size for Use in the Determination of mRNA by Competitive PCR"; *PCR Methods and Applications*, 4:219–226 (1995).

Clementi et al.; "Quantitative PCR and RT–PCR in Virology"; *PCR Methods and Applications*, 2:191–196 (1993).

F. Ferre; "Quantitative or Semi–Quantitative PCR: Reality Versus Myth"; *PCR Methods and Applications*, 2:1–9 (1992).

M. Piatak, Jr., et al., "Research Report. Quantitative Competitive Polymerase Chain Reaction for Accurate Quantitation of HIV DNA and RNA Species," *BioTechniques* 14(1), pp. 70–80 (1993).

G. Haberhausen et al., "Comparative Study of Different Standardization Concepts in Quantitative Competitive Reverse Transcription–PCR Assays," *Journal of Clinical Microbiology* 36(3), pp. 628–633 (Mar. 1998).

L. Raeymaekers, "Quantitative PCR: Theoretical Considerations with Practical Implications," *Analytical Biochemistry* 214, pp. 582–585 (1993).

L. Raeymaekers, "A Commentary on the Practical Applications of Competitive PCR," *Genome Research* 5, pp. 91–94 (1995).

Tan et al.; "PAF and TNF Increase the Precursor of NF–kappa B p50 mRNA in Mouse Intestine: Quantitative Analysis by Competitive PCR"; *Biochimica et Biophysica Acta*, 1215:157–162 (1994).

Kellogg et al.; "Quantitation of HIV–1 Proviral DNA Relative to Cellular DNA by the Polymerase Chain Reaction"; *Analytical Biochemistry*, 189:202–208 (1990).

Holland et al.; "Detection of specific polymerase chain reaction product by utilizing the 5' → 3' exonuclease activity of thermus aquaticus DNA polymerase"; *Proc. Natl. Acad. Sci. USA*, 88:7276–7280 (1991).

Walker et al.; "Isothermal in vitro amplification of DNA by a restriction enzyme/DNA polymerase system"; *Proc. Natl. Acad. Sci. USA*, 89:392–296 (1992).

Furtado et al.; "Changes in the Viral mRNA Expression Pattern Correlate with a Rapid Rate of $CD4_+$ T–Cell Number Decline in Human Immunodeficiency Virus Type 1–Infected Individuals"; *J. of Virology*, 69(4):2092–2100 (1995).

Kwoh et al.; "Transcription–based amplification system and detection of amplified human immunodeficiency virus type 1 with a bead–based sandwich hybridization format"; *Proc. Natl. Acad. Sci. USA*, 86:1173–1177 (1989).

(List continued on next page.)

*Primary Examiner*—Kenneth R. Horlick
*Assistant Examiner*—Janell E. Taylor
*Attorney, Agent, or Firm*—Donna R. Fugit

[57] ABSTRACT

Methods for determining quantities of nucleic acid sequences in samples undergoing amplification utilize amplification ratio estimates (R*) in operations to accurately perform absolute quantitation even when amplification factors for the target and control sequences undergoing amplification are different, time dependent or vary as a function of starting concentrations of nucleic acid sequences. These operations also take into account conversion efficiencies associated with the conversion of probes upon generation of target or control amplicons, but do not require the explicit calculation of such efficiencies. The operations also recognize that a preferred R* should be determined based on a preferred statistical criterion to improve quantitation. In addition, the use of standard samples having known starting concentrations of target and control sequences therein may enable accurate absolute quantitation without the explicit calculation of amplification ratio estimates.

45 Claims, 6 Drawing Sheets

OTHER PUBLICATIONS

Pang et al.; "High levels of unintegrated HIV-1 DNA in brain tissue of AIDS dementia patients"; *Nature*, 343:85–89 (1990).

Lizardi et al.; "Experonential Amplification of Recombinant-RNA Hybridization Probes"; *Bio/Technology*, 6:1197–1202 (1988).

Slamon et al.; "Human Breast Cancer: Correlation of Relapse and Survival with Amplification of the HER-2/neu Oncogene"; *Science*, 235:177–182 (1987).

Sooknanan et al.; "NASBA: A Detection and Amplification System Uniquely Suited for RNA"; *Bio/Technology*, 13:563–564 (1995).

Piatak et al.; "High Levels of HIV-1 ijn Plasma During All Stages of Infection Determined by Competitive PCR"; *Science*, 259:1749–1754 (1993).

METHODS, APPARATUS AND COMPUTER PROGRAM PRODUCTS FOR DETERMINING QUANTITIES OF NUCLEIC ACID SEQUENCES IN SAMPLES USING STANDARD CURVES AND AMPLIFICATION RATIO ESTIMATES

FIELD OF THE INVENTION

This invention relates to methods, apparatus and computer program products for characterizing nucleic acid sequences, and more particularly to methods, apparatus and computer program products for determining quantities of nucleic acid sequences in samples.

BACKGROUND OF THE INVENTION

Quantitative nucleic sequence analysis plays an increasingly important role in the fields of biological and medical research. For example, quantitative gene analysis has been used to determine the genome quantity of a particular gene, as in the case of the human HER-2 oncogene which is found at amplified levels in approximately 30% of human breast cancers. D. J. Slamon et al., *Science* 235, 177–182 (1987). More recently, gene and genome quantitation have also been used in determining and monitoring the levels of human immunodeficiency virus (HIV) in patients throughout the different phases of HIV infection and disease. M. R. Furtado et al., *J. Virol.* 69, 2092–2100 (1995). It has been suggested that higher levels of circulating HIV and failure to effectively control virus replication after infection may be associated with a negative disease prognosis; in other words, there may be an association between virus level (HIV replication) and the pathogenesis of the disease. M. Paitak et al., *Science* 259, 1749–1754 (1993). Accordingly, an accurate determination of HIV nucleic acid levels early in an infection may serve as a useful tool in diagnosing illness, while the ability to correctly monitor changing levels of viral nucleic acid throughout the course of an illness may provide clinicians with critical information regarding the effectiveness of treatment and progression of disease. Additionally, the determination of virion-associated HIV RNA levels in plasma represents a marker of viral replication with potential widespread applicability in assessment of the activity of antiretroviral therapy. ld.

Several methods have been described for the quantitative analysis of nucleic acid sequences. The polymerase chain reaction (PCR) and reverse-transcriptase PCR (RT-PCR) have permitted the analysis of small starting quantities of nucleic acid (e.g., as little as one cell equivalent). See, e.g., S. Edmands et al. 1994, PCR *Methods Applic.* 3, 317–19; I. R. Rodriguez et al. 1992, *Nucleic Acids Res.* 20, 3528. Early reports of quantitative PCR report quantitation of the PCR product, but do not directly measure the initial target sequence quantity. F. Ferre 1992, PCR *Methods Applic.* 2, 1–9. In general, these methods involve measuring PCR product at the end of nonisothermal amplification and relating this endpoint measurement level back to the starting nucleic acid concentration. Unfortunately, the absolute amount of product generated does not always bear a consistent and easily quantifiable relationship to the amount of target sequence present at the initiation of the amplification reaction. The kinetics and efficiency of amplification of a target nucleic acid sequence may also be strongly dependent on the starting abundance of the target sequence and the sequence match of the primers and target template. Thus, some RT-PCR amplification methods which rely on "endpoint" analysis may be capable of only revealing the presence or absence of the target nucleic acid sequence, but not the actual starting quantity with any degree of accuracy. For these reasons, comparison of the amount of specimen-derived PCR product to the amount of product from a separately amplified external control standard typically does not provide a highly accurate basis for quantitation.

One specific approach to nucleic acid amplification using PCR measures product quantity in the log phase of the reaction prior to the plateau. See, e.g., Kellogg et al. 1990, *Anal. Biochem.* 189, 202–208; S. Pang et al. 1990, *Nature* 343, 85–89. This method requires that each sample have equal input amounts of nucleic acid sequence and that each sample under analysis amplifies with identical efficiency up to the point of quantitative analysis. A gene sequence (contained in all samples at a relatively constant quantity) can be used for sample amplification efficiency normalization. However, using conventional methods of PCR detection and quantitation, it may be extremely laborious to assure that all samples are analyzed during the log phase of the reaction, both for the target gene and the normalization gene.

Another method referred to as quantitative competitive PCR (QC-PCR) has also been developed and is now widely used for PCR quantitation. See, e.g., P. D. Siebert and J. W Larrick 1992, *Nature* 359, 557–558; and X. Tan et al. 1994, *Biochim. Biophys. Acta* 1215, 157–162. QC-PCR relies on the inclusion of a known amount of an internal control competitor in each reaction mixture. The efficiency of each reaction is also normalized to the internal competitor. To obtain relative quantitation, the unknown target PCR product is compared with the known competitor PCR product, usually via gel electrophoresis. The relative amount of target-specific and competitor DNA is measured and used to calculate the starting number of target templates. Basically, in this kind of analysis, the larger the ratio of target specific product to competitor specific product, the higher the starting DNA concentration.

However, articles by Luc Raeymaekers, entitled "A Commentary on the Practical Applications of Competitive PCR", *Genome Research* 5, pp. 91–94 (1995) and "Quantitative PCR: Theoretical Considerations with Practical Implications" *Analytical Biochemistry* 214, pp. 582–585 (1993) (hereinafter, the "Raeymaekers 1995" and "Raeymaekers 1993" articles), suggest that PCR, by itself, may not be an accurate quantitation assay, notwithstanding its extreme sensitivity and specificity relative to other methods based on probe hybridization. In particular, because of the many amplification steps which take place during PCR, small differences in amplification efficiency may result in dramatic differences in product yield. Furthermore, because the exponential phase of the reaction is of limited duration (because of the accumulation of product), if PCR is run beyond the exponential phase into the saturation phase when endpoint analysis is performed, initial differences in the amount of template may become obscured. To compensate for some of these intrinsic difficulties associated with accurate quantitation using PCR, controls have been introduced. However, these controls may not adequately account for specific pitfalls associated with QC-PCR which uses an external standard sequence to facilitate quantitation.

As explained at page 92 of the Raeymaekers 1995 article, the prefix "QC" in QC-PCR refers to the fact that competition occurs between target and standard templates for available substrates when PCR is allowed to proceed into the saturation phase. Because the sum of the masses of both products cannot exceed some maximum value, the amount of product formed from one template will decrease with the increasing quantity of the other template. As will be understood by those skilled in the art, the products of target and standard sequences are discriminated either by a difference in length or by a specific restriction site in the region between the primer templates. In practice, a plurality of PCR tubes containing the same but unknown amount of target sequence is spiked with a dilution series of defined quantities of the standard. If the amplification factor is the same for both sequences, their ratio will remain constant during amplification and the amount of the unknown template can then be accurately quantitated from the ratio of the two products. Raeymaekers recommends that a "curve" be generated which relates the logarithm of the ratio of PCR products standard/target to the logarithm of the initial known amount of standard cDNA added (i.e., log $(T_n/S_n)$ versus log $(S_0)$). Here, Raeymaekers uses a plurality of samples and each sample has an aliquot portion of an unknown quantity of target and a respective known quantity of standard (S). The amount of initial target can then be read from the point on the curve where the amounts of target (T) and standard (S) are equal (i.e., where S/T=1 or log (S/T)=0).

Raeymakers also explains that if there is a difference in the amplification factor, theory predicts a parallel shift of the curve. This shift will cause a displacement in the point of equivalence and a faulty quantification because the magnitude of the displacement typically cannot be detected (because a reference point is typically not available). According to Raeymaekers, any determination that the curve has a slope of −1 does not suggest that the amplification factors are the same for both target and standard. From these considerations, Raeymaekers concludes that if a PCR assay yields a curve relating log $(T_n/S_n)$ to log $(S_0)$ which is not linear or does not have a slope of −1 (or +1 in the event the abscissa provides log $(T_0)$), it cannot be used for either absolute or relative quantitation. Moreover, the slope =−1 requirement for the curve is a necessary but not a sufficient condition for establishing that the amplification factors are the same for T and S and therefore not a sufficient condition for absolute quantitation. Instead, the requirement that the amplification factors are equal has to be independently demonstrated as a prerequisite to obtaining accurate absolute quantitation, without reliance on the curve, and such independent demonstration may be difficult to achieve particularly if the target and standard sequences are dissimilar. These conclusions are explained more fully at pages 584 and 92 of the Raeymaekers 1993 and 1995 articles, respectively.

Similar conclusions are also reached at page 632 of an article by G. Haberhausen et al., entitled "Comparative Study of Different Standardization Concepts in Quantitative competitive Reverse Transcription-PCR Assays" Journal of Clinical Microbiology, Vol. 36, No. 3, pp. 628–633 (1998). Finally, the attempts at quantitation which are illustrated by the curves of FIGS. 2, 4 and 6 of an article by M. Piatak et al., entitled "Quantitative Competitive Polymerase Chain Reaction for Accurate Quantitation of HIV DNA and RNA Species", BioTechniques, Vol. 14, No. 1, pp. 70–80 (1993), would appear to be flawed in view of Raeymaekers' conclusions and further because the absolute values of the slopes of these curves differ significantly from unity. The accuracy of the results of Piatak et al. which are predicted from "corrected" fluorescence indicia may also be limited because the indicia were not obtained in real-time during amplification, but only after termination of amplification.

Thus, notwithstanding these attempts to perform absolute quantitation using nonisothermal amplification techniques such as PCR, there continues to a be need for improved methods of accurately determining starting quantities of nucleic acid sequences undergoing amplification, which do not require the establishment of identical amplification factors as a prerequisite to performing absolute quantitation.

SUMMARY OF THE INVENTION

It is therefore an object of the present invention to provide improved methods, apparatus and computer program products for determining starting quantities of nucleic acid target sequences in test samples undergoing nucleic acid amplification.

It is also an object of the present invention to provide methods, apparatus and computer program products for more accurately measuring absolute quantities of nucleic acid target sequences in test samples containing known starting quantities of nucleic acid control sequences therein, even if the amplification factors for the target and control sequences undergoing amplification are different and dependent on time and the starting concentrations of the target and control sequences.

It is still another object of the present invention to provide improved methods, apparatus and computer program products for performing absolute quantitation of nucleic acids undergoing isothermal amplification using methods such as Strand Displacement Amplification (SDA).

These and other objects, features and advantages are provided, according to the present invention, by methods, apparatus and computer program products for performing absolute quantitation of starting quantities of nucleic acid target sequences in test samples containing respective known starting quantities of a nucleic acid control sequence therein. These operations to perform absolute quantitation may use amplification ratio estimates which take into account differences in amplification and related factors (e.g., detection efficiency) associated with competitive amplification of nucleic acid control and target sequences using nucleic acid amplification methods which include isothermal amplification.

According to one preferred embodiment of the present invention, a plurality of standard samples and at least one test sample are formed. The plurality of standard samples each contain a known starting quantity of a nucleic acid control sequence and a known starting quantity of a nucleic acid target sequence therein. The starting concentrations of the nucleic acid control sequence in the standard samples are also preferably set to equal levels to improve quantitation accuracy. The test sample contains a known starting quantity of the nucleic acid control sequence and an unknown starting quantity of the nucleic acid target sequence therein. The nucleic acid sequences in these standard samples and test sample are then amplified, preferably in parallel, during an amplification time interval. These sequences may be amplified using a preferred isothermal reaction method such as Strand Displacement Amplification (SDA), however, a thermal cycling reaction method such as Polymerase Chain Reaction (PCR), may also be used. According to a preferred aspect of the present invention, the isothermal reaction method utilizes two differentially labeled detector probes (signal primers). One probe is specific for target sequences being amplified (i.e., target amplicons) and the other probe is specific for control sequences being amplified (i.e., control amplicons). During the amplification reaction, each detector probe binds to its specific amplicon and is then converted to a cleaved form which preferably exhibits a much higher fluorescence intensity than the unconverted form of the probe.

Indicia of the amplified quantities of the nucleic acid control and target sequences in each of the standard samples and in the test sample are then measured in real-time, preferably at respective measurement time intervals (which may be normalized to respective measurement time points) in the amplification time interval if a real-time amplification method such as SDA is utilized. The indicia of the quantities of the nucleic acid control and target sequences being amplified may take the form of fluorescence signals (e.g., fluorescence intensities or detectable fluorescent energy transfers) if the samples contain fluorescent indicators therein (e.g., fluorescent dyes, labels, intercalators, etc). For example, during each of a plurality of consecutive measurement time intervals within the amplification time interval, a plurality of fluorescence measurements may be performed on the plurality of control and test samples. However, other indicia which are suitable for real-time measurement (e.g., radioactive signals) may also be used instead of fluorescence.

The measured indicia may then be collected over a range of measurement time intervals as respective normalized target fluorescence and normalized control fluorescence curves (i.e., $NF_T(t)$ and $NF_c(t)$). For example, using mathematical techniques well known to those skilled in the art, fluorescence measurements for all measurement time intervals may be analyzed and then normalized to respective measurement time points within the amplification time interval. Thus, if the normalized control fluorescence curves are generated as a two-dimensional graph, for example, the measurement time points may be assigned along the abscissa of the graph and the normalized fluorescence values may be assigned along the ordinate of the graph. Preferred operations are then performed to determine an amplification ratio (R*) from the measured indicia of the amplified quantities of the nucleic acid control and target sequences in the standard samples. A magnitude of the starting quantity of the nucleic acid sequence in the test sample is then determined in a preferred manner from the amplification ratio and the measured indicia of the amplified quantities of the nucleic acid control and target sequences in the test sample.

The operations to determine the amplification ratio assume that during amplification the number of nucleic acid control amplicons at time "t" (i.e., $C(t)$) and the number of nucleic acid target amplicons at time "t" (i.e., $T(t)$) can be determined with a good degree of accuracy from the following relationship: $\log (T(t)/C(t)r) = \log (T_0) - \log(C_0)$, where $C_0$ and $T_0$ represent the starting quantities of the nucleic acid control and target sequences in a respective control or test sample, respectively, "r" represents the ratio of the target amplification factor to the control amplification factor (i.e., $r = (\exp^{\lambda_T t}/\exp^{\lambda_c t})$), and $\lambda_T$ and $\lambda_c$ represent the amplification rates for the target and control sequences.

Operations to determine the amplification ratio may also utilize the following preferred relationships: $T(t)\eta_T/N_p = (NF_T(t) - NF_T|_{base})/\Delta_T$ and $C(t)\eta_c/N_p = (NF_c(t) - NF_c|_{base})/\Delta_c$, where $N_p$ equals the starting number of probes, $\eta_T$ equals the number of probes converted for every target amplicon generated, $\eta_c$ equals the number of probes converted for every control amplicon generated, $\Delta_T$ equals ($NF_T|_{max} - NF_T|_{base}$) and $\Delta_c$ equals ($NF_c|_{max} - NF_c|_{base}$), where $NF_{T,c}|_{max}$ represents a maximum fluorescence signal if all probes were converted. From these relationships, a comprehensive relationship for absolute quantitation can be determined as: $\log [((NF_T(t) - NF_T|_{base})\eta_c\Delta_c)/((NF_c(t) - NF_c|_{base})\eta_T\Delta_T r)] = \log (T_0) - \log (C_0)$, where the amplification ratio R* represents ($\eta_T\Delta_T r/\eta_c\Delta_c$).

The operations to determine an amplification ratio R* in a preferred manner do not require the separate determination of $\eta_T$, $\Delta_T$, r, $\eta_c$ and $\Delta_c$. The operations also recognize that R* may vary as a function of time "t", $T_0$ and $C_0$, and that a preferred R*(t) should be determined based on a preferred statistical criterion. In particular, operations are performed to determine respective amplification ratios from indicia measurements performed during respective measurement time intervals within the amplification time interval, and then determine, relative to a statistical criterion, which of the amplification ratios better satisfies the statistical criterion against known starting quantities of the nucleic target sequences in the standard samples. These respective amplification ratios may also be determined as an average of amplification ratios for a number of selected standard samples, with each ratio for each of the selected standard samples being determined at each of the measurement time points. For example, measurement indicia from two or more standard samples having identical starting quantities of control and target sequences ($C_0, T_0$) therein may be used to determine a respective average amplification ratio corresponding to measurement indicia obtained during a respective measurement time interval. In particular, the operations of the present invention preferably generate a set of amplification ratios $\{\overline{R}_1^*, \overline{R}_2^*, \overline{R}_3^*, \overline{R}_4^*, \ldots, \overline{R}_n^*\}$ with each ratio being an average value based on control samples having identical starting quantities of control and target sequences therein, for example, and also corresponding to an effective measurement time point along the abscissa of the graphs of $NF_T(t)$ and $NF_c(t)$).

According to another preferred embodiment of the present invention, operations for explicitly determining amplification ratio estimates may be bypassed by utilizing the measured indicia from the plurality of standard samples to predict a best "time" to perform absolute quantitation. In particular, a statistical criterion, such as a conventional fit-to-line statistical criterion, may be applied to relationships between measured fluorescence indicia (at various time points within the amplification time interval) and the starting quantities of the nucleic acid target sequence in the standard samples, to determine a most preferred relationship upon which to base absolute quantitation. These relationships preferably take the form of $\log [(NF_T(t) - NF_T|_{base})/(NF_c(t) - NF_c|_{base})]$ versus $\log (T_0)$.

Still another preferred embodiment of the present invention includes an apparatus for determining a quantity of a nucleic acid sequence in a test sample. This preferred apparatus comprises means, such as a fluorescence measurement tool, for measuring indicia of quantities of nucleic acid target and control sequences being amplified in a test sample, which contains an unknown starting quantity of the nucleic acid target sequence and a known starting quantity of the nucleic acid control sequence therein, and in a plurality of standard samples which each contain respective known starting quantities of the nucleic acid control and target sequences therein. A computer program product is also provided for controlling operation of the measuring means and performing numerical calculations to carry out the above-described operations.

In particular, a preferred computer program product comprises a computer readable storage medium having computer-readable program code means embodied in the medium. The preferred computer-readable program code means comprises computer-readable program code means for determining an amplification ratio from the measured indicia of the amplified quantities of the nucleic acid control and target sequences in the standard samples. Computer-readable program code means is also provided for determining a magnitude of the starting quantity of the nucleic acid target sequence in the test sample from the amplification ratio and the measured indicia of the amplified quantities of the nucleic acid control and target sequences in the test sample. In addition, computer-readable program code means is also provided for performing more detailed ones of the above-described operations numerically. This embodiment of the present invention therefore provides a tool which can more accurately perform absolute quantitation to determine starting quantities of nucleic acid target sequences in test samples, even if the amplification factors for the target and control sequences undergoing amplification are different and/or time dependent. These computer program products may be realized in whole or in part as software modules running on a computer system. Alternatively, a dedicated stand-alone system with application specific integrated circuits for performing the above described operations may be provided.

DESCRIPTION OF PREFERRED EMBODIMENTS

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
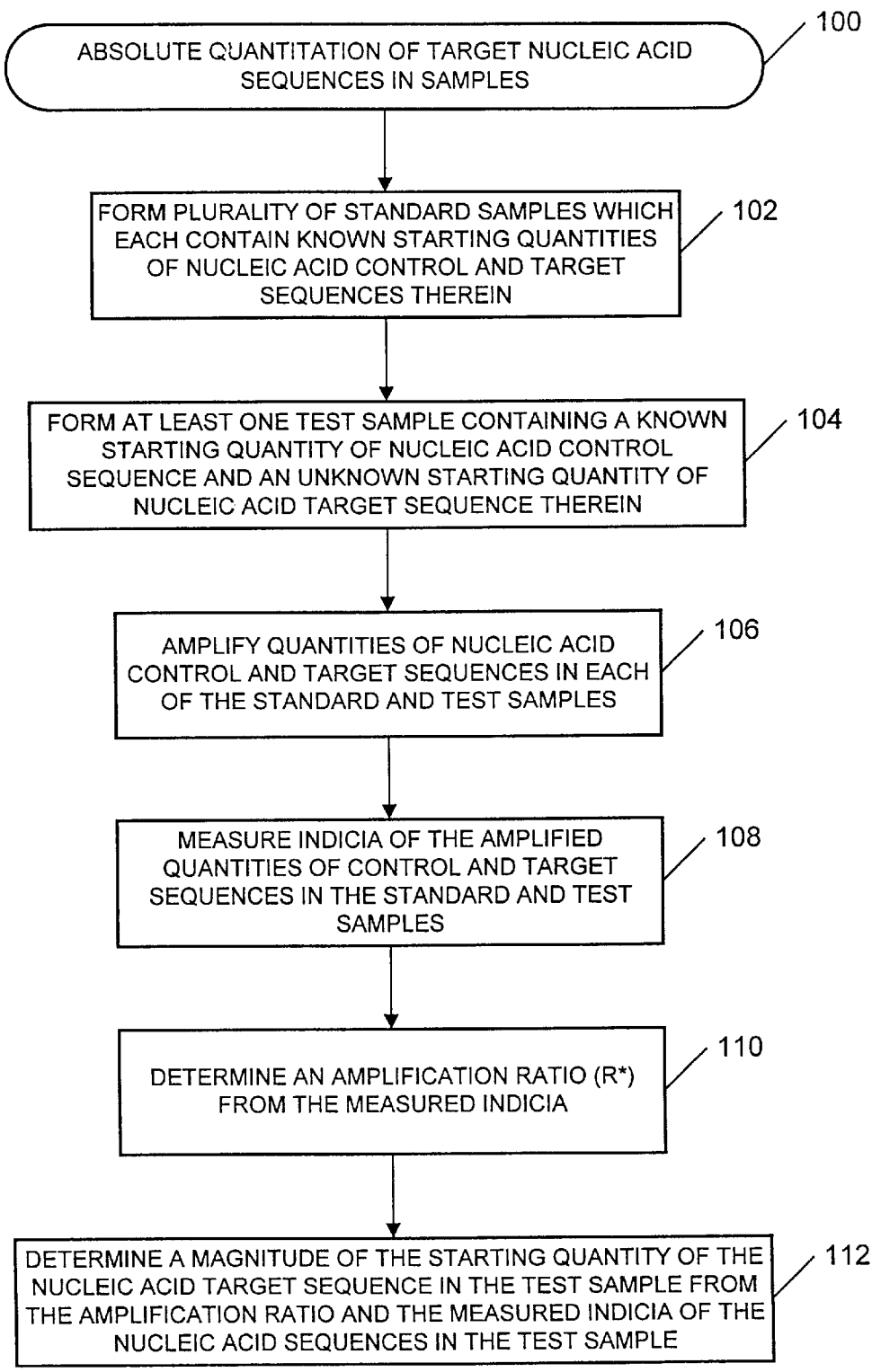
FIG. 1 is a flow chart illustrating operations performed by methods, apparatus and computer program products according to a first embodiment the present invention.

Referring now to FIG. 1, preferred operations 100 for performing absolute quantitation of starting quantities of nucleic acid target sequences (e.g., RNA, DNA) in test samples use amplification ratio estimates. These amplification ratio estimates take into account differences in amplification and related factors (e.g., detection efficiency) associated with competitive amplification of nucleic acid control and target sequences. According to a preferred embodiment of the present invention, a plurality of standard samples and at least one test sample are initially formed, Blocks 102 and 104. The plurality of standard samples each contain a known starting quantity of a nucleic acid control sequence and a known (and different) starting quantity of a nucleic acid target sequence therein and the test sample contains a known starting quantity of the nucleic acid control sequence and an unknown starting quantity of the nucleic acid target sequence therein. It is this unknown starting quantity of the nucleic acid target sequence that is to be determined by absolute quantitation. The starting concentrations of the nucleic acid control sequence in the standard samples are also preferably set to equal known levels to enable quantitation.

The nucleic acid sequences in these standard samples and test sample are then preferably amplified in parallel during an amplification time interval, Block 106. Alternatively, the amplification operations may be performed separately for each of the samples during respective nonoverlapping time intervals. These separate time intervals may then be normalized to a common starting time and time interval for purposes of analysis. As will be understood by those skilled in the art, the samples may be amplified according to any known nucleic acid amplification methods, including both thermal cycling amplification methods and isothermal amplification methods. The present invention can enhance absolute quantitation of nucleic acids amplified by either thermal cycling methods or isothermal methods, although the present invention may provide particular advantages to isothermal amplification methods.

Suitable thermal cycling methods useful in the practice of the present invention include, but are not limited to, the Polymerase Chain Reaction (PCR) (see, U.S Pat. Nos. 4,683,202, 4,683,195 and 4,965,188); Reverse Transcriptase PCR (RT-PCR); DNA Ligase Chain Reaction (LCR) (see, International Patent Application No. WO 89109835); and transcription-based amplification (see, e.g., D. Y. Kwoh et al. 1989, *Proc. Natl. Acad. Sci.* USA 86, 1173–1177). Suitable isothermal amplification methods useful in the practice of the present invention include, but are not limited to, Strand Displacement Amplification (SDA) (see, e.g., Walker et al. 1992, *Proc. Natl. Acad. Sci.* USA 89, 392–396); Qβ replicase (Lizardi et al. 1988, *Bio/Technology* 6, 1197–1202); Nucleic Acid-Based Sequence Amplification (NASBA; R. Sooknanan and L. Malek 1995, *Bio/Technology* 13, 563–65); and Self-Sustained Sequence Replication (3SR; Guatelli et al. 1990, *Proc. Natl. Acad. Sci.* USA 87, 1874–1878). Exemplary SDA methods are also described in U.S. Pat. Nos. 5,445,166 to Walker and 5,270,184 to Walker et al., the disclosures of which are hereby incorporated herein by reference.

The isothermal reaction method may utilize two differentially labeled detector probes (signal primers). One probe is specific for target sequences being amplified (i.e., target amplicons) and the other probe is specific for control sequences being amplified (i.e., control amplicons). During the amplification reaction, each detector probe binds to its specific amplicon and is then converted to a cleaved form which preferably exhibits a much higher fluorescence intensity than the unconverted form of the probe. These and other aspects associated with a preferred isothermal reaction method are more fully described in U.S. Pat. No. 5,547,861 to Nadeau et al., entitled "Detection of Nucleic Acid Amplification"; U.S. application Ser. No. 08/865,675, to Nadeau et al., filed May 30, 1997, entitled "Detection of Nucleic Acid Sequences by Fluorescence Quenching" (Attorney Docket No. P-3746); and U.S. application Ser. No. 08/855,085, to Nadeau et al., filed May 13, 1997, entitled "Detection of Nucleic Acids by Fluorescence Quenching" (Attorney Docket No. P-3747); assigned to the present assignee, the disclosures of which are hereby incorporated herein by reference.

Indicia of the amplified quantities of the nucleic acid control and target sequences in each of the standard samples and in the test sample are then measured, preferably at respective measurement time intervals in the amplification time interval if a real-time amplification method such as SDA is utilized, Block 108. These measurements may be made by a microwell plate fluorescence measurement tool such as the CytoFluor Series 4000 from PerSeptive Biosystems. The Model 7700 Sequence Detector, manufactured and distributed by Applied Biosystems, a division of Perkin Elmer, Foster City, Calif., may also be used as a measurement tool. The indicia of the quantities of the nucleic acid control and target sequences being amplified may take the form of fluorescence signals (e.g., fluorescence intensities or detectable fluorescent energy transfers) if the samples contain fluorescent indicators therein (e.g., fluorescent dyes, labels, intercalators, etc). Accordingly, the measurement tool may contain one or more photodetectors for measuring the fluorescence signals from the samples undergoing parallel amplification. The measurement tool may also contain a computer-controlled stepper motor so that the control and test samples can be arranged as an array of samples and automatically and repeatedly positioned opposite a photodetector upon measurement of fluorescence intensity. A preferred measurement tool is more fully described hereinbelow with reference to FIG. 6. Thus, during each of a plurality of consecutive measurement time intervals within the amplification time interval, a plurality of fluorescence measurements may be obtained from the plurality of control and test samples. Using techniques well known to those skilled in the art, the fluorescence measurements made during a respective measurement time interval may also be normalized to respective measurement time points.

Other indicia which are suitable for real-time measurement (e.g., radioactive signals) may also be used instead of fluorescence. For example, indicia of nucleic acid concentration may be provided by labels that produce signals detectable by fluorescence, radioactivity, colorimetry, X-ray diffraction or absorption, magnetism, or enzymatic activity. Chemiluminescence and fluorescence lifetime measurements may also be utilized. Suitable labels include, fluorophores, chromophores, radioactive isotopes (e.g., $^{32}P$ or $^{125}I$), electron-dense reagents, enzymes, and ligands having specific binding partners (e.g., biotin-avidin). Labeling of nucleic acids may be achieved by a number of means, including chemical modification of a nucleic acid primer or probe. Suitable fluorescent labels may include non-covalently binding labels (e.g., intercalating dyes) such as ethidium bromide, propidium bromide, chromomycin, acridine orange, and the like. However, the use of covalently bound fluorescent agents is preferred in the present invention. Such covalently bound fluorescent labels include fluorescein and derivatives thereof such as FAM, HEX, TET and JOE (all of which can be obtained from the Applied Biosystems Division of Perkin Elmer, Foster City, Calif.); rhodamine and derivatives such as Texas Red (Molecular Probes, Eugene, Oreg.); ROX and TAMRA (Applied Biosystems, Foster City, Calif.); Lucifer Yellow; coumarin derivatives and the like. Another preferred indicia of nucleic acid concentration is fluorescence energy-transfer (FET), in which a fluorescent reporter (or "donor") label and a quencher (or "acceptor") label are used in tandem to produce a detectable signal that is proportional to the amount of amplified nucleic acid product (e.g., in the form of double-stranded nucleic acid) present in the reaction mixture. Yet another detection method is fluorescence polarization (FP) detection of nucleic acid amplification, as described in U.S. Pat. No. 5,593,867 to Walker et al., assigned to the present assignee, the disclosure of which is hereby incorporated herein by reference. Fluorescence lifetime measurements may be made by a microwell fluorescence reader such as Flowstar, manufactured by BMG. Chemiluminescence measurements may be made by a luminometer such as the Luminoskan, manufactured by Labsystems. Radioactivity measurements may be made by a scintillation counter, such as the Beckman LS6500.

The measured indicia may then be collected over a plurality of consecutive measurement time intervals and processed to generate respective normalized target fluorescence and normalized control fluorescence curves (i.e., $NF_T(t)$ and $NF_c(t)$). For example, the fluorescence measurements for all measurement time intervals may be analyzed and then normalized to respective measurement time points and if the normalized control fluorescence curves are generated as a two-dimensional graph, the measurement time points may be assigned to the abscissa of the graph and the normalized fluorescence values may be assigned to the ordinate of the graph.

Figure 2:
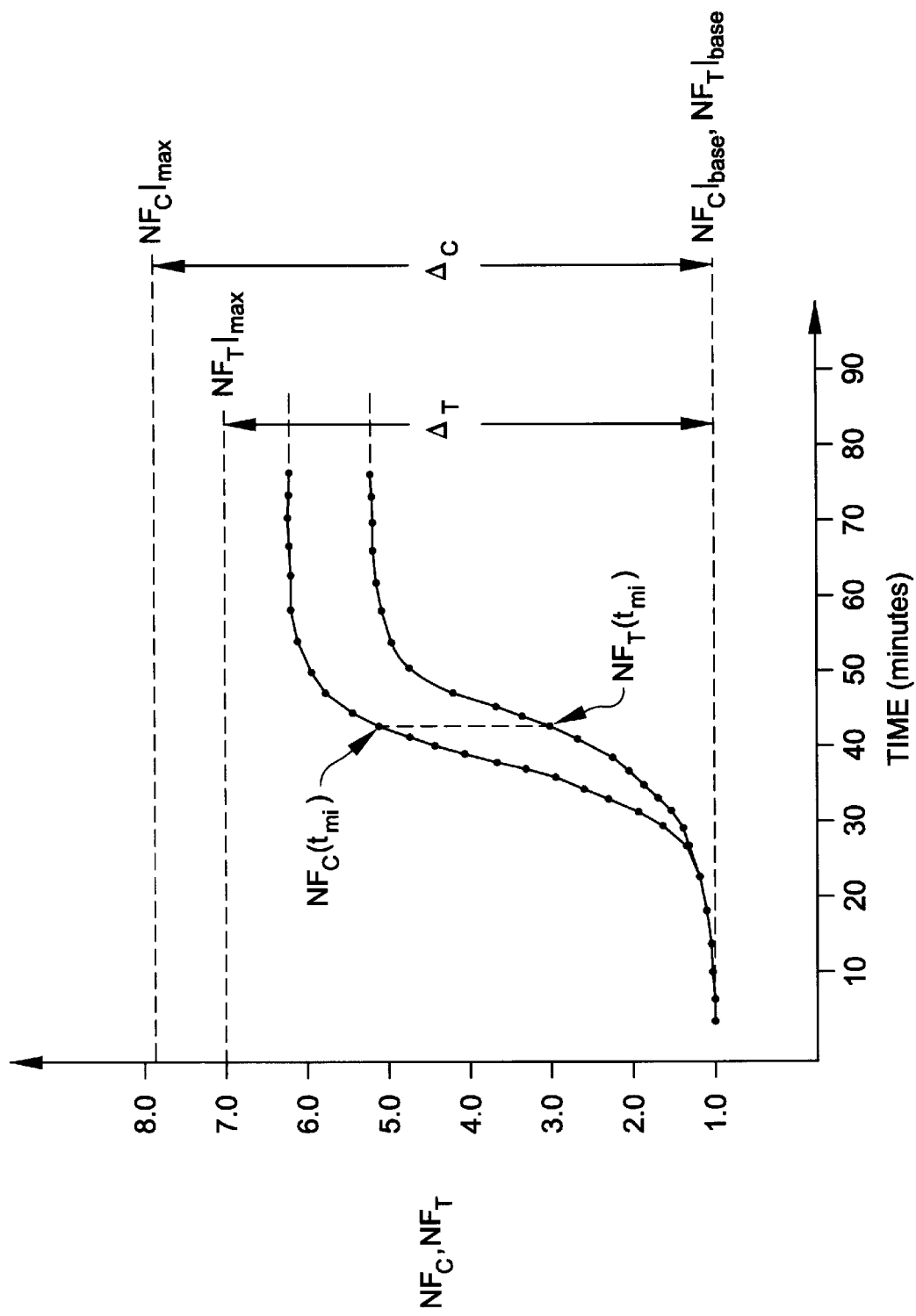
FIG. 2 is a graph of normalized fluorescence curves $NF_c(t)$ and $NF_T(t)$ corresponding to a standard or test sample containing amplified quantities of control and target nucleic acid sequences therein.

For example, FIG. 2 is a graph of normalized fluorescence curves $NF_c(t)$ and $NF_T(t)$ corresponding to a standard or test sample containing amplified quantities of control sequence ($C_n$) and target nucleic acid sequence ($T_n$) therein, where "n" represents the sample number. The normalized value of 1.0 on the y-axis of FIG. 2 represents $NF_c|_{base}$ and $NF_T|_{base}$, and $\Delta_T$ and $\Delta_c$ equal $(NF_T(t)|_{max} - NF_T|_{base})$ and $(NF_c(t)|_{max} - NF_c|_{base})$, respectively. Additional details associated with the generation and analysis of normalized target fluorescence and normalized control fluorescence curves (i.e., $NF_T(t)$ and $NF_c(t)$, where "N" denotes "normalized") are provided in copending U.S. application Ser. No. 08/862,905, to Haaland, filed May 23, 1997, entitled "Methods, Apparatus and Computer Program Products for Determining Quantities of Nucleic Acid Sequences in Samples" (Attorney Docket No. P-3892), assigned to the present assignee, the disclosure of which is hereby incorporated herein by reference. As will be understood by those skilled in the art, the use of normalized data is preferred for facilitating higher accuracy quantitation, but is not absolutely necessary.

Referring again to FIG. 1, preferred operations are then performed to determine an amplification ratio (R*) from the measured indicia of the amplified quantities of the nucleic acid control and target sequences in the standard samples, Block 110. A magnitude of the starting quantity of the nucleic acid sequence in the test sample is then determined in a preferred manner from the amplification ratio and the measured indicia of the amplified quantities of the nucleic acid control and target sequences in the test sample, Block 112. The operations to determine the amplification ratio assume that during amplification, the number of nucleic acid control amplicons at time "t" (i.e., C(t)) and the number of nucleic acid target amplicons at time "t" (i.e., T(t)) can be determined with a good degree of accuracy from the following relationship:

$$\log (T(t)/C(t)r) = \log (T_0) - \log (C_0) \quad (1)$$

where $C_0$ and $T_0$ represent the starting quantities of the nucleic acid control and target sequences in a respective control or test sample, respectively, and "r" represents the ratio of the target amplification factor to the control amplification factor. As evident by equation (1), any variation in "r" will influence the y-intercept associated with a graph of $\log (T(t)/C(t)r)$ versus $\log (T_0)$. As will be understood by those skilled in the art, the ratio of the target amplification factor to the control amplification factor is typically expressed as:

$$r = (\exp^{\lambda_T t}/\exp^{\lambda_c t}) \tag{2}$$

where $\lambda_T$ and $\lambda_c$ represent the amplification rates for the target and control sequences during amplification.

Operations to determine the amplification ratio also utilize the following preferred relationship which can be obtained from FIG. 2 and an understanding of the amplification method:

$$T(t)\eta_T/N_P = (NF_T(t) - NF_T|_{base})\Delta_T \tag{3}$$

$$C(t)\eta_c/N_P = (NF_c(t) - NF_c|_{base})\Delta_c \tag{4}$$

where $N_P$ equals the starting number of probes, $\eta_T$ equals the number of probes converted for every target amplicon generated, $\eta_c$ equals the number of probes converted for every control amplicon generated. As described above with respect to FIG. 2, $\Delta_T$ equals $(NF_T(t)|_{max} - NF_T|_{base})$ and $\Delta_c$ equals $(NF_c(t)|_{max} - NF_c|_{base})$ From these relationships, a comprehensive relationship for absolute quantitation can be determined as:

$$\log\left[((NF_T(t) - NF_T|_{base})\eta_c\Delta_c)/((NF_c(t) - NF_c|_{base})\eta_T\Delta_T r)\right] = \log(T_0) - \log(C_0) \tag{5}$$

where, $$R^* = \eta_T \Delta_T r / \eta_c \Delta_c \tag{6}$$

The operations described below to determine an amplification ratio R* in a preferred manner do not require the separate and computationally expensive determination of $\eta_T$, $\Delta_T$, r, $\eta_c$ and $\Delta_c$ which may be functionally dependent on time and the starting concentrations $T_0$ and $C_0$. Moreover, the amplification ratio R* is not equivalent to the statistical fit-to-line correlation factor R and $R^2$ illustrated by FIGS. 2–6 of the aforementioned Piatak et al. article. The preferred operations also recognize that R* may vary as a function of time "t" (and the starting concentrations $T_0$ and $C_0$) and that a preferred R*(t) should be determined based on a preferred statistical criterion (e.g., fit-to-line). Here, the reference to a "preferred" R*(t) may also be considered as a recognition that there exists a preferred point in time during amplification where $R^*(t, T_0, C_0)$ changes systematically to yield a curve of points which best approximates a straight line, as illustrated and described more fully hereinbelow with respect to FIG. 3.

In particular, operations are performed to determine respective amplification ratios from indicia measurements performed during respective measurement time intervals within the amplification time interval, and then determine, relative to a statistical criterion, which of the amplification ratios better satisfies the statistical criterion against known starting quantities of the nucleic acid target sequences in the standard samples. To improve quantitation, these respective amplification ratios R* may also be determined as an average of amplification ratios determined for a number of selected standard samples, with each ratio for each of the selected standard samples being determined at each of the normalized measurement time points. These operations will now be described.

In particular, an amplification ratio $R^*(t_{mi})$ may be determined for a respective sample by combining equations (5) and (6) to yield:

$$\log\left[(NF_T(t) - 1)/()NF_c(t) - 1)R^*\right] = \log(T_0) - \log(C_0) \tag{7}$$

where $NF_c|_{base}$ and $NF_T|_{base}$ have been set to the normalized value of 1.0 (see, e.g., y-axis of FIG. 2) and $t_{mi}$ represents a respective normalized measurement time point on the x-axis of FIG. 2. By forming a first standard sample with equal starting quantities of nucleic acid control sequence and target sequence therein (i.e., $T_0 = C_0$), a first amplification ratio corresponding to the first starting sample can be determined from FIG. 2 as:

$$R^*(t_{mi}) = (NF_T(t_{mi}) - 1)/(NF_c(t_{mi}) - 1) \tag{8}$$

Operations are then performed which use the first estimated amplification ratio $R^*(t_{mi})$ to determine a plurality of log-log relationships (e.g., x-y graphs), with each log-log relationship corresponding to a respective time point in the plurality of time points $t_{mi}$. Each of these log-log relationships includes a respective data point for each of the standard samples (where $T_0$ is known). In particular, the log-log relationships may be determined as respective x-y graphs by plotting, for each respective $t_{mi}$, the left side of equation (7) versus log ($T_0$), using the corresponding first estimated amplification ratio $R^*(t_{mi})$.

As will be understood by those skilled in the art, each x-y graph will provide a curve of points with the number of points being equal to the number of standard samples. Conventional line-fitting algorithms can then be used to generate, for each graph, a line having a positive slope, for example. As explained more fully hereinbelow, a "best" line (corresponding to a "best" $t_{mi}$) can then be determined using a statistical criterion, and then the magnitude of the starting quantity of the nucleic acid target sequence in the test sample can be determined from the "best" line by calculating the left side of equation (7) for the test sample at the "best" $t_{mi}$ and then reading the corresponding value of log ($T_0$) off the line.

Figure 3:
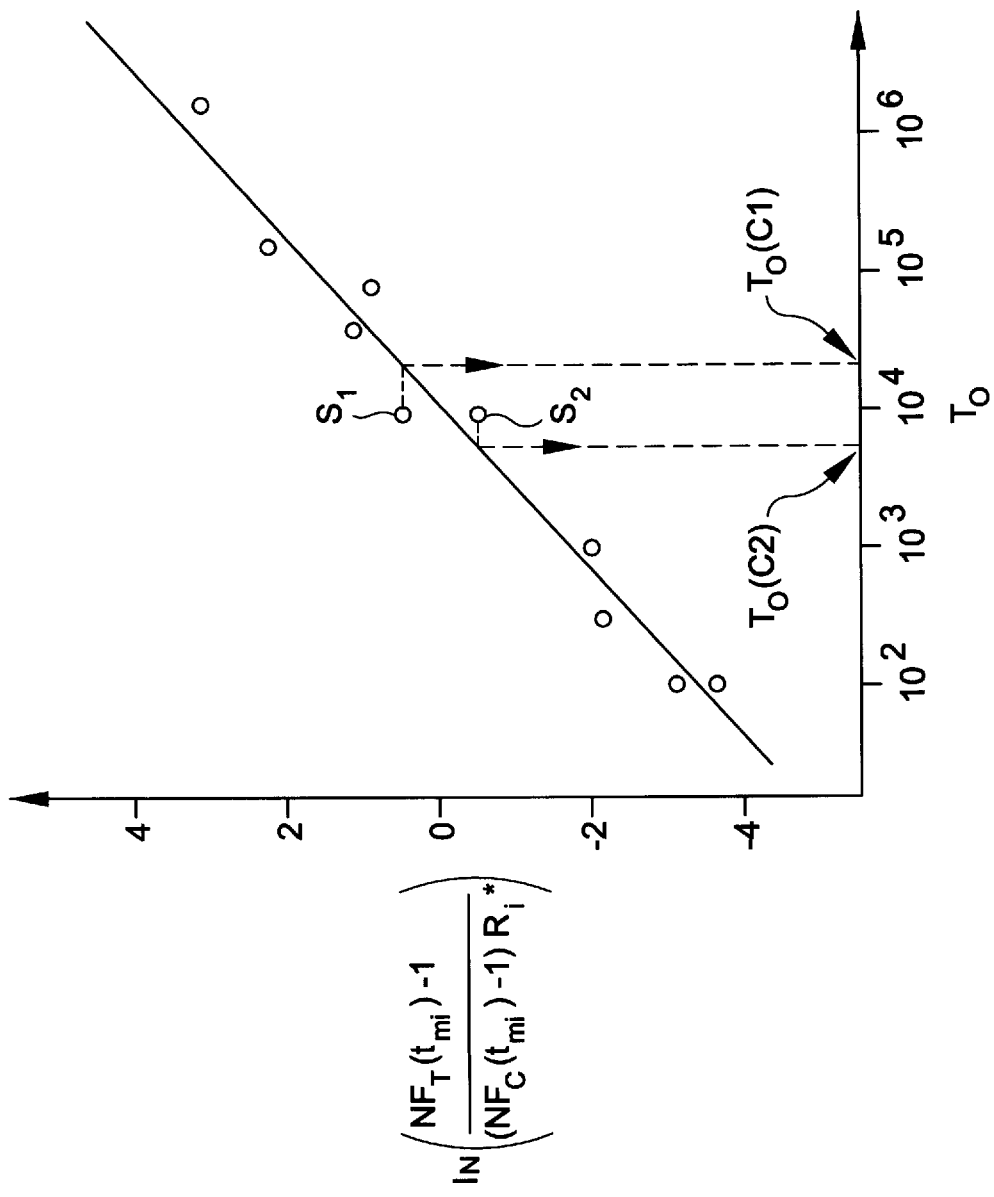
FIG. 3 is a graph of log $[(NF_T(t_{mi})-1)/(NF_c(t_{mi})-1)R_i^*]$ verus log $(T_0)$ which facilitates determination of a magnitude of a starting quantity of a nucleic acid target sequence in a test sample.

Referring now to FIG. 3, the "best" line may also be determined from a "best" average amplification ratio $\bar{R}^*_i(t_{mi})$ by using an exemplary statistical criterion (fit-to-line) which will now be described. In particular, for each $t_{mi}$, a corresponding average amplification ratio $\bar{R}_i$ is determined using measurement indicia obtained from two (or more) standard samples ($S_1$ and $S_2$) which each have identical starting quantities of nucleic acid target and control sequences therein (i.e., $C_0 = T_0$). As illustrated by the following relationships, a set of average amplification ratios can be generated as $\{\bar{R}_1, \bar{R}_2, \bar{R}_3, \ldots, \bar{R}_i\}$:

$$\bar{R}_1^* = (R^*(t_{m1})|_{S1} + R^*(t_{m1})|_{S2})/2 \tag{9.1}$$

$$\bar{R}_2^* = (R^*(t_{m2})|_{S1} + R^*(t_{m2})|_{S2})/2 \tag{9.2}$$

$$\bar{R}_3^* = (R^*(t_{m3})|_{S1} + R^*(t_{m3})|_{S2})/2 \tag{9.3}$$

$$\bar{R}_i^* = (R^*(t_{mi})|_{S1} + R^*(t_{mi})|_{S2})/2 \tag{9.i}$$

Then, a respective x-y graph can be obtained for each $t_{mi}$, as illustrated by FIG. 3, with each data point corresponding to a respective standard sample (including points corresponding to $S_1$ and $S_2$ which have the same x-value). A conventional line fitting algorithm can then be used to fit a corresponding line through the data points in each x-y graph. Then, because two of the standard samples have identical starting quantities of target and control sequences therein, the "calculated" magnitudes of the starting quantities of the nucleic acid target sequences in the two standard samples can be determined by using each line to read respective logarithms of these calculated magnitudes off each x-axis. These calculated magnitudes are illustrated as $T_0(C1)$ and $T_0(C2)$ on FIG. 3. Operations are then performed to determine which of the measurement time points $t_{mi}$ yields "calculated" magnitudes which are closest to the known starting quantity of the nucleic acid target sequence in the two standard samples. For example, an average calculated magnitude can be determined by averaging the two calculated magnitudes $T_0(C1)$ and $T_0(C2)$ and then determining which average calculated magnitude is closest to the known starting quantity. The line which yields the closest average calculation is then used to determine the starting quantity of the nucleic acid target sequence in the test sample. This line corresponds to the "best" $t_{mi}$ at which absolute quantitation should be performed to yield accurate results, notwithstanding the fact that the amplification factors associated with the target and control sequences are different.

According to another preferred embodiment of the present invention, operations for explicitly determining amplification ratio estimates may be bypassed by utilizing the measured indicia from the plurality of standard samples to directly predict a best "time" to perform absolute quantitation. In particular, a statistical criterion, such as a conventional fit-to-line statistical criterion, may be applied to relationships between measured fluorescence indicia (at various time points within the amplification time interval) and the starting quantities of the nucleic acid target sequence in the standard samples, to determine a most preferred relationship upon which to base absolute quantitation. These relationships preferably take the form of log $[NF_T(t) - NF_T|_{base})/(NF_c|_{base})]$ versus log $(T_0)$, where $NF_T|_{base}$ and $NF_c|_{base}$ may be set to unity as illustrated by FIG. 2.

Figure 4:
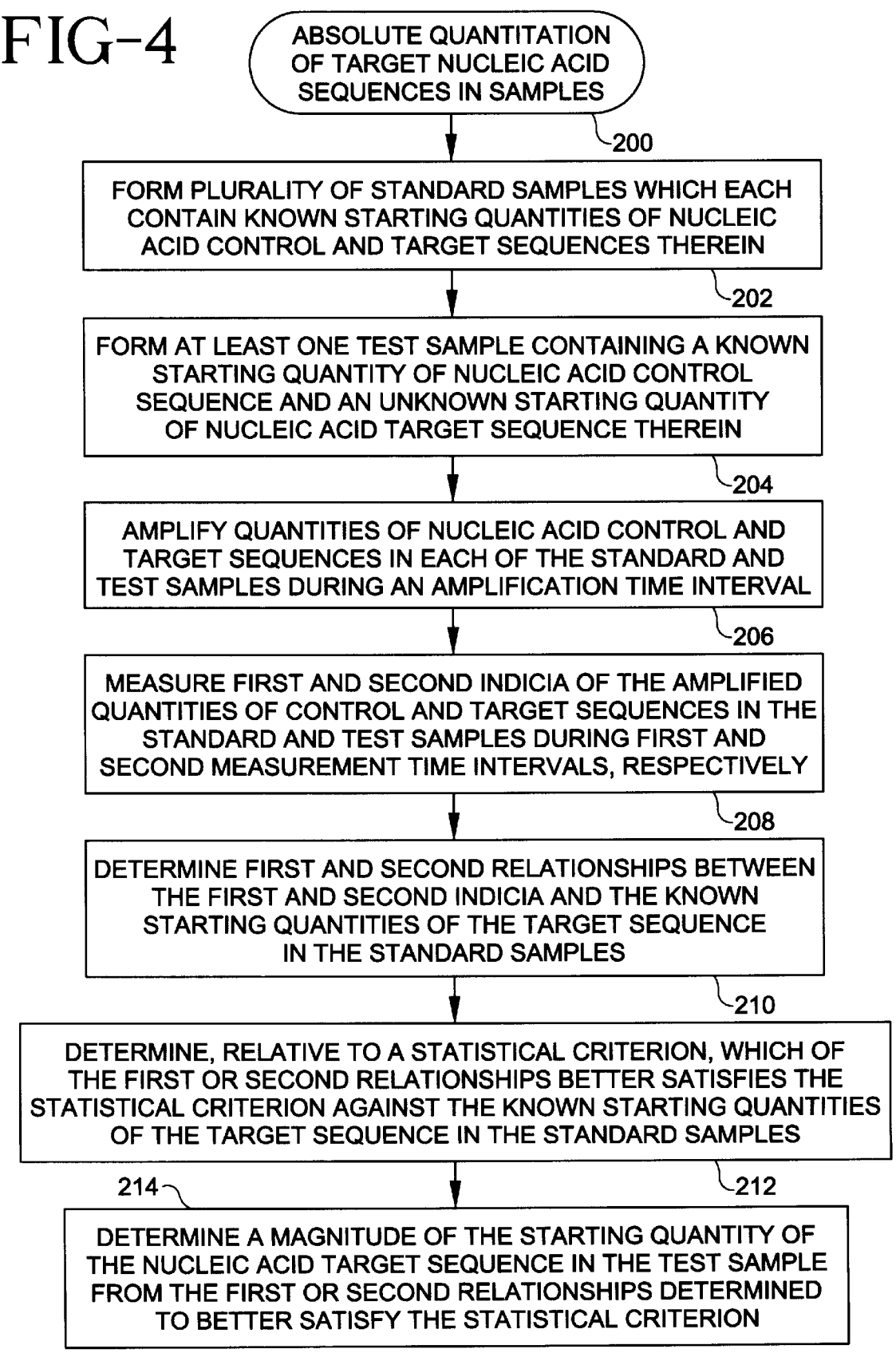
FIG. 4 is a flow chart illustrating operations performed by methods, apparatus and computer program products according to a second embodiment the present invention.

In particular, FIG. 4 illustrates preferred operations 200 for performing absolute quantitation of starting quantities of nucleic acid target sequences (e.g., RNA, DNA) in test samples by analyzing standard curves. These standard curves are determined from indicia measured in real-time during amplification from standard samples containing known starting quantities of control and target sequences therein (with the known starting quantities of the control sequence preferably being the same in each of the standard samples). For example, according to this alternative embodiment, a plurality of standard samples and at least one test sample are initially formed, Blocks 202 and 204. The plurality of standard samples each contain a known starting quantity of a nucleic acid control sequence and a known starting quantity of a nucleic acid target sequence therein and the test sample contains a known starting quantity of the nucleic acid control sequence and an unknown starting quantity of the nucleic acid target sequence therein. The nucleic acid sequences in these standard samples and test sample are then preferably amplified in parallel during an amplification time interval, Block 206. Multiple sets of indicia (e.g., fluorescence indicia) of the amplified quantities of the nucleic acid control and target sequences in each of the standard samples and in the test sample are then measured in real-time, preferably at respective measurement time intervals within the amplification time interval if an amplification method such as SDA is preferably utilized, Block 208. Accordingly, during each of a plurality of consecutive measurement time intervals within the amplification time interval, a plurality of fluorescence measurements may be obtained from the plurality of control and test samples. The measured indicia may then be collected over a plurality of consecutive measurement time intervals and processed to generate respective normalized target fluorescence and normalized control fluorescence curves (i.e., $NF_T(t)$ and $NF_c(t)$) for each of the samples. For example, like the first embodiment, the fluorescence measurements for all measurement time intervals may be analyzed and then normalized to respective measurement time points and if the normalized control fluorescence curves are generated as a two-dimensional graph, the measurement time points may be assigned to the abscissa of the graph and the normalized fluorescence values may be assigned to the ordinate of the graph, as illustrated best by FIG. 2.

Figure 5:
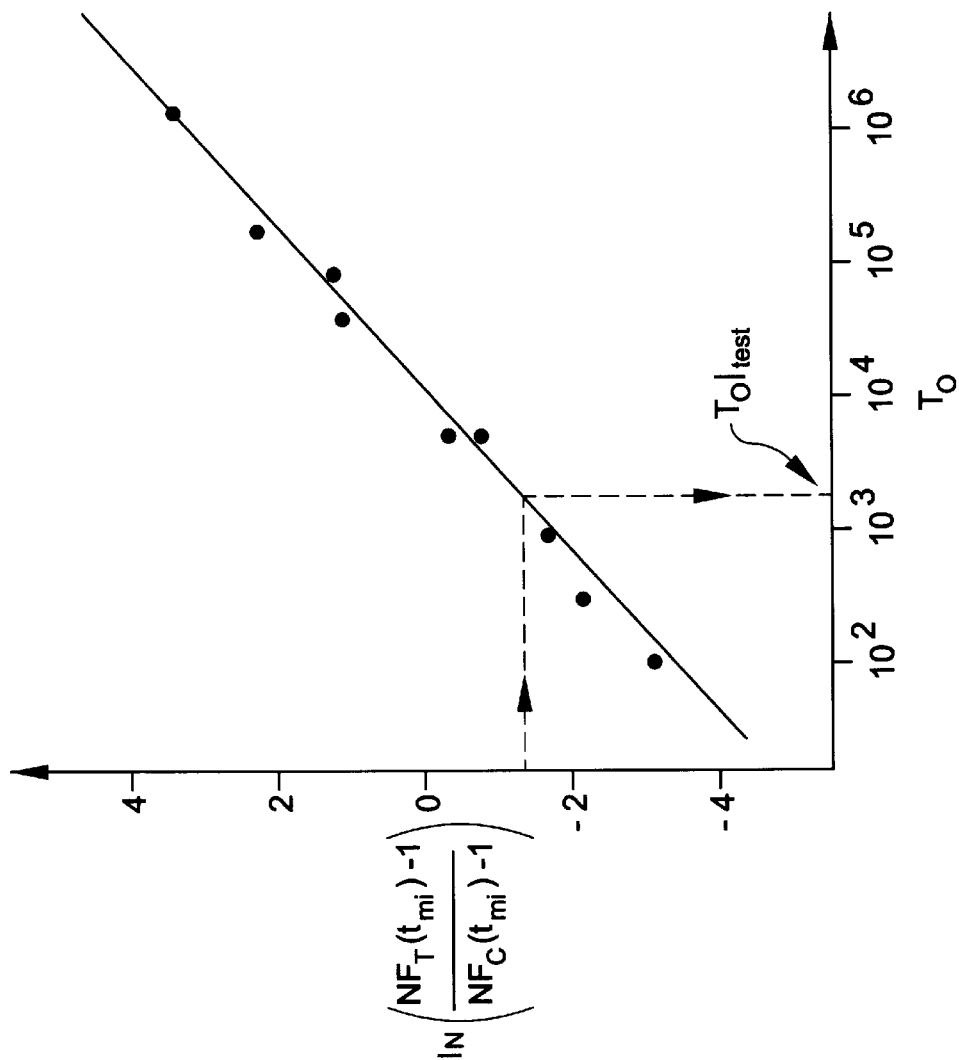
FIG. 5 is a graph of log $[(NF_T(t_{mi})-1)/(NF_c(t_{mi})-1)]$ verus log $(T_0)$ which facilitates determination of a magnitude of a starting quantity of a nucleic acid target sequence in a test sample.

Referring still to FIG. 4, operations are then performed to determine respective relationships between the measured indicia and the known starting quantities of the target sequence in the standard samples, Block 210, at each of a plurality of measurement time points in the amplification time interval (e.g., $t_{m1}, t_{m2}, \ldots, t_{mi}$). These relationships may take the form of respective x-y graphs of $\log[(NF_T(t_{m1}) - NF_T|_{base})(NF_c(t_{m1}) - NF_c|_{base})]$ versus $\log(T_0)$ for each of the plurality of standard samples. An exemplary x-y graph derived from fluorescence measurements made for each of the standard samples at a respective time point $t_{mi}$ is illustrated by FIG. 5. Each graph contains a curve of discrete points with each point corresponding to a standard sample.

Operations are then performed at Block 212 to determine, relative to a statistical criterion, which of the first or second relationships better satisfies the statistical criterion against the known starting quantities of the target sequence in the plurality of standard samples. For example, with respect to first and second curves of discrete points of the type illustrated by FIG. 5, these operations may include operations to fit the first curve to a first line and fit the second curve to a second line and determine which of the first and second lines provides a better statistical fit to its respective curve. Here, the operations to determine which of the first and second lines provides a better statistical fit may include the operations of determining a first "T-value" as the slope of the first line divided by a standard error in the slope of the first line, determining a second "T-value" as the slope of the second line divided by a standard error in the slope of the second line and then selecting the curve which results in the largest T-value. The line corresponding to the selected curve is then used to determine a magnitude of the starting quantity of the nucleic acid target sequence in the test sample $(T_0|_{test})$, Block 214.

Figure 6:
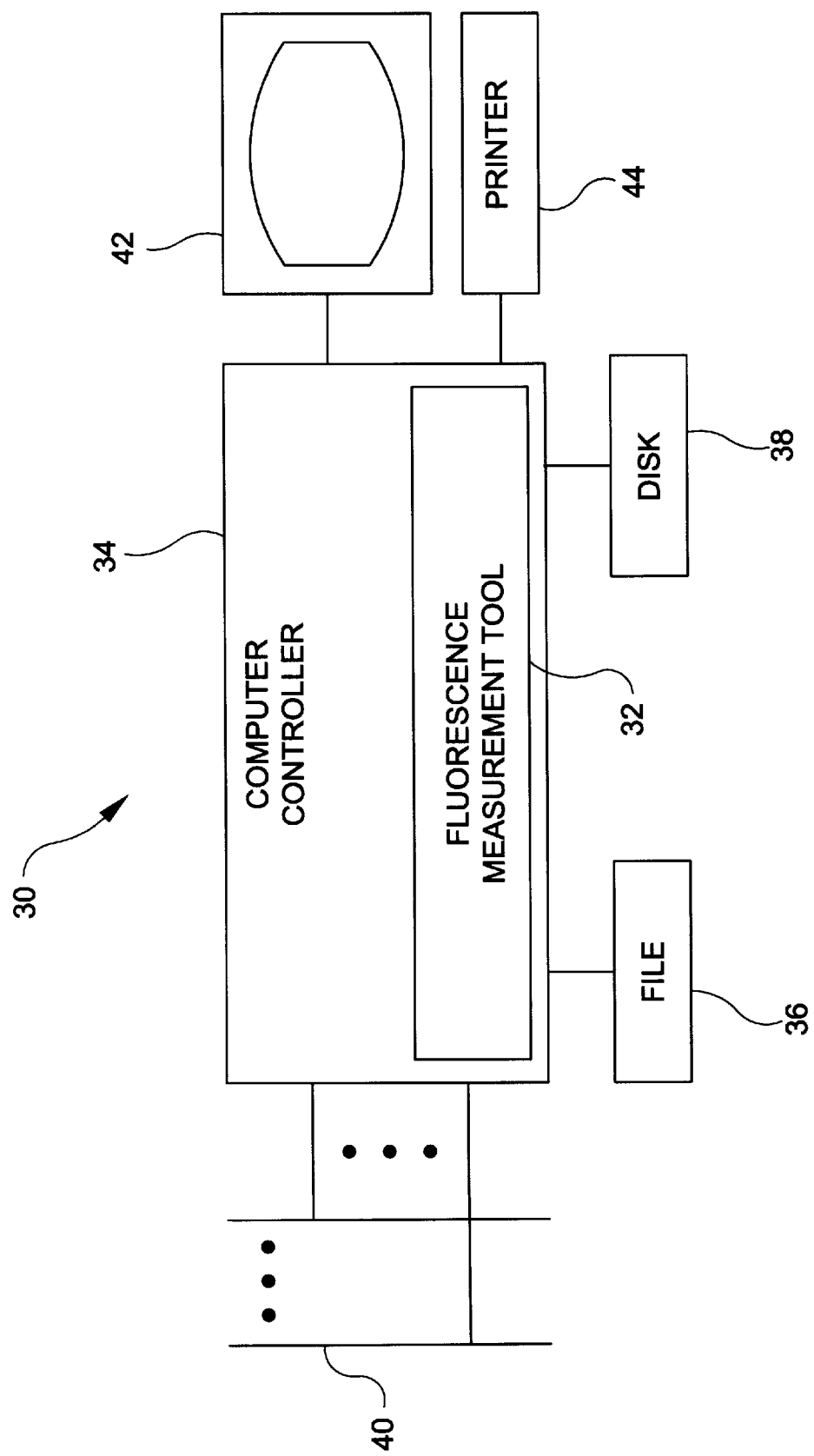
FIG. 6 illustrates a general hardware description of apparatus for determining quantities of nucleic acid sequences in test samples, according to the present invention.

Another preferred embodiment of the present invention includes an apparatus 30 for determining quantities of nucleic acid target sequences in test samples, as illustrated by FIG. 6. This preferred apparatus comprises means 32, such as the aforementioned fluorescence measurement tool, for measuring indicia of quantities of nucleic acid target and control sequences being amplified in a test sample and being amplified in a plurality of standard samples. The apparatus 30 also operates under computer control. In particular, the measurement tool 32 is preferably operatively coupled to a general purpose or application specific computer controller 34. The controller 34 preferably comprises a computer program product(s) for controlling operation of the measurement tool 32 and performing numerical operations relating to the above-described steps. The controller 34 may accept set-up and other related data via a file 36, disk input 38 or data bus 40. A display 42 and printer 44 are also preferably provided to visually display the operations performed by the controller 34.

It will be understood by those having skill in the art that the functions performed by the controller 34 may be realized in whole or in part as software modules running on a general purpose computer system. Alternatively, a dedicated stand-alone system with application specific integrated circuits for performing the above described functions and operations may be provided. In particular, a preferred computer program product will comprise a computer readable storage medium having computer-readable program code means embodied in the medium. The preferred computer-readable program code means comprises computer-readable program code means for performing the operations described with respect to FIGS. 1 and 4 and throughout the present description.

In the drawings and specification, there have been disclosed typical preferred embodiments of the invention and, although specific terms are employed, they are used in a generic and descriptive sense only and not for purposes of limitation, the scope of the invention being set forth in the following claims. Moreover, the terminology in the present description and claims relating to graphs, plotting lines, determining linear relationships, determining "best" times, calculated magnitudes, etc. is intended to include the processing of data and variables internal to a processing unit (e.g., computer) containing memory and not limited to the physical acts of printing or plotting lines, curves, and graphs. The functions $F_T(t)$ and $(F_c(t)$ and the constants $F_T|_{base}$ and $F_c|_{base}$, as used in the claims, are also inclusive of respective functions and constants obtained using normalized data (i.e., $NF_T(t)$, $NF_c(t)$, $NF_T|_{base}$ and $NF_c|_{base}$).

That which is claimed is:

1. A method of determining a quantity of a nucleic acid sequence in a sample, comprising the steps of:
   forming a plurality of standard samples which each contain a known starting quantity of a nucleic acid control sequence and a known starting quantity of a nucleic acid target sequence therein;
   forming a test sample containing a known starting quantity of the nucleic acid control sequence and an unknown starting quantity of the nucleic acid target sequence;
   amplifying quantities of the nucleic acid control and target sequences in each of the standard samples and the test sample, during an amplification time interval;
   measuring first and second indicia of the amplified quantities of the nucleic acid control and target sequences in each of the standard samples during first and second measurement time intervals, respectively;
   measuring indicia of the amplified quantities of the nucleic acid control and target sequences in the test sample;
   determining first and second amplification ratios from the first and second measured indicia of the amplified quantities of the nucleic acid control and the target sequences in the standard samples; and
   determining a magnitude of the starting quantity of the nucleic acid target sequence in the test sample from the first or second amplification ratio and the measured indicia of the amplified quantities of the nucleic acid control and target sequences in the test sample.

2. The method of claim 1, wherein said measuring step is performed during the amplification time interval.

3. The method of claim 2, wherein said step of determining a magnitude comprises determining, relative to a statistical criterion, which of the first and second amplification ratios better satisfies the statistical criterion against the known starting quantities of the nucleic acid target sequence in the standard samples.

4. The method of claim 3, wherein said step of determining a magnitude comprises determining a magnitude of the starting quantity of the nucleic acid target sequence in the test sample from the first or second amplification ratio determined to better satisfy the statistical criterion.

5. The method of claim 1, wherein said step of forming a plurality of standard samples comprises forming a first standard sample containing equal starting quantities of nucleic acid control and target sequences therein.

6. The method of claim 5, wherein said step of determining an amplification ratio comprises determining an amplification ratio from measured indicia of the amplified quantities of the nucleic acid control and target sequences in the first standard sample.

7. The method of claim 6, wherein said measuring step comprises the step of measuring control and target fluorescence intensities which are a function of the amplified quantities of the nucleic acid control and target sequences in the first standard sample, respectively.

8. The method of claim 7, wherein said step of determining an amplification ratio comprises the steps of:
   determining control and target fluorescence relationships $(F_c(t))$ and $(F_T(t))$ as a function of time (t) for the first standard sample, from the measured control and target fluorescence intensities; and
   determining an amplification ratio ($R^*$) based on the following relationship (where $C_0$ and $T_0$ represent the equal starting quantities of the nucleic acid control and target sequences in the first standard sample, respectively): $\log[(F_T(t)-F_T|_{base})/((F_c(t)-F_c|_{base})R^*)] = \log T_0 - \log C_0$.

9. The method of claim 1, wherein said step of forming a plurality of standard samples comprises forming first and second standard samples which each contain equal starting quantities of nucleic acid control and target sequences therein; and wherein said measuring step comprises measuring first indicia of the amplified quantities of the nucleic acid control and target sequences in each of the standard samples and test sample during a first measurement time interval.

10. The method of claim 9, wherein said step of determining an amplification ratio comprises the steps of:
   determining a first amplification ratio from the measured first indicia of the amplified quantities of the nucleic acid control and target sequences in the first standard sample;
   determining a second amplification ratio from the measured first indicia of the amplified quantities of the nucleic acid control and target sequences in the second standard sample; and
   averaging the first and second amplification ratios to obtain a first average amplification ratio ($\overline{R}_1^*$).

11. The method of claim 10, wherein said step of forming a plurality of standard samples comprises forming a third standard sample having unequal starting quantities of the nucleic acid control and target sequences therein; and wherein said measuring step comprises measuring control and target fluorescence intensities which are a function of the amplified quantities of the nucleic acid control and target sequences in the third standard sample, during the first measurement time interval.

12. The method of claim 11, wherein said step of determining a magnitude comprises the steps of:
   determining control and target fluorescence relationships $(F_c(t))$ and $(F_T(t))$ as a function of time (t) for the third standard sample, from the measured control and target fluorescence intensities; and
   determining a relationship between $(F_T(t)-F_T|_{base})/((F_c(t)-F_c|_{base}) \overline{R}_1^*)$ and $T_0$, where $T_0$ represents the starting quantity of the nucleic acid target sequence in the third standard sample.

13. The method of claim 12, wherein said step of determining a relationship comprises determining $\log[(F_T(t)-F_T|_{base})/((F_c(t)-F_c|_{base}) \overline{R}_1^*)]$ versus $\log(T_0)$.

14. The method of claim 10, wherein said measuring step comprises measuring second indicia of the amplified quantities of the nucleic acid control and target sequences in each of the standard samples and test sample during a second measurement time interval; and wherein said step of determining an amplification ratio comprises the steps of:

determining a third amplification ratio from the measured second indicia of the amplified quantities of the nucleic acid control and target sequences in the first standard sample;

determining a fourth amplification ratio from the measured second indicia of the amplified quantities of the nucleic acid control and target sequences in the second standard sample; and averaging the third and fourth amplification ratios to obtain a second average amplification ratio ($\overline{R}_2^*$).

15. The method of claim 14, wherein said step of determining a magnitude comprises the steps of:

determining, relative to a statistical criterion, which of the first and second average amplification ratios ($\overline{R}_1^*$) and ($\overline{R}_2^*$) better satisfies the statistical criterion against the known starting quantities of the nucleic acid target sequence in the first and second standard samples; and determining a magnitude of the starting quantity of the nucleic acid target sequence in the test sample from the first or second average amplification ratio determined to better satisfy the statistical criterion.

16. The method of claim 6, wherein said measuring step comprises measuring control and target fluorescence intensities which are a function of the amplified quantities of the nucleic acid control and target sequences in the plurality of standard samples and test sample, during first and second measurement time intervals.

17. The method of claim 16, wherein said step of determining an amplification ratio comprises the steps of:

determining respective control and target fluorescence relationships ($F_c(t)$) and ($F_T(t)$) as a function of time (t) for the plurality of standard samples and test sample, from the measured control and target fluorescence intensities; and determining an amplification ratio ($R^*$) based on the following relationship (where $C1_0$ and $T1_0$ represent the equal starting quantities of the nucleic acid control and target sequences in the first standard sample, respectively): $\log[(F_T(t)-F_T|_{base})/((F_c(t)-F_c|_{base}) R^*)] = \log T1_0 - \log C1_0$; and wherein said step of determining a magnitude comprises determining a linear relationship between $(F_T(t)-F_T|_{base})/((F_c(t)-F_c|_{base})R^*)$ and $Tn_0$, where $Tn_0$ represents the starting quantities of the nucleic acid target sequence in the plurality of standard samples.

18. The method of claim 17, wherein said step of determining a magnitude comprises determining the magnitude of the starting quantity of the nucleic acid target sequence in the test sample from the linear relationship.

19. The method of claim 1, wherein said measuring step comprises measuring control and target fluorescence intensities which are a function of the amplified quantities of the nucleic acid control and target sequences in a first standard sample; and wherein said step of determining an amplification ratio comprises the steps of:

determining control and target fluorescence relationships ($F_c(t)$) and ($F_T(t)$) as a function of time (t) for the first standard sample, from the measured control and target fluorescence intensities; and determining an amplification ratio ($R^*$) based on the following relationship (where $C_0$ and $T_0$ represent the starting quantities of the nucleic acid control and target sequences in the first standard sample, respectively): $\log[(F_T(t)-F_T|_{base})/((F_c(t)-F_c|_{base})R^*)] = \log T_0 - \log C_0$.

20. A method of determining a quantity of a nucleic acid sequence in a sample, comprising the steps of:

forming a plurality of standard samples which each contain a known starting quantity of a nucleic acid control sequence and a known starting quantity of a nucleic acid target sequence therein;

forming a test sample containing a known starting quantity of the nucleic acid control sequence and an unknown starting quantity of the nucleic acid target sequence;

amplifying quantities of the nucleic acid control and target sequences in the standard samples and test sample, during an amplification time interval;

measuring first and second indicia of the amplified quantities of the nucleic acid control and target sequences in the standard samples and test sample, during first and second measurement time intervals, respectively;

determining a first relationship between the first indicia and the known starting quantities of the nucleic acid target sequence in the standard samples;

determining a second relationship between the second indicia and the known starting quantities of the nucleic acid target sequence in the standard samples;

determining, relative to a statistical criterion, which of the first and second relationships better satisfies the statistical criterion against the known starting quantities of the nucleic acid target sequences in the standard samples; and determining a magnitude of the starting quantity of the nucleic acid target sequence in the test sample from the first or second relationship determined to better satisfy the statistical criterion.

21. The method of claim 20, wherein the first and second measurement time intervals are respective nonoverlapping time intervals within the amplification time interval.

22. The method of claim 21, wherein said measuring step comprises:

measuring first indicia as first control and target fluorescence intensities which are a function of the amplified quantities of the nucleic acid control and target sequences in the plurality of standard samples; and measuring second indicia as second control and target fluorescence intensities which are a function of the amplified quantities of the nucleic acid control and target sequences in the plurality of standard samples.

23. The method of claim 22, further comprising the step of determining control and target fluorescence relationships ($F_c(t)$) and ($F_T(t)$) as a function of time (t) within the amplification time interval, from the measured first and second indicia.

24. The method of claim 23, wherein the plurality of standard samples have equal starting quantities of nucleic acid control sequence therein; wherein said step of determining a first relationship comprises determining a first set of points from $\log[(F_T(t_{m1})-F_T|_{base})/(F_c(t_{m1})-F_c|_{base})]$ versus $\log(T_0)$ for each of the plurality of standard samples, where $T_0$ represents the starting quantity of the nucleic acid target sequence in a respective standard sample and $t_{m1}$ represents a first time point in the amplification time interval; and wherein said step of determining a second relationship comprises determining a second set of points from $\log[(F_T(t_{m2})-F_T|_{base})/(F_c(t_{m2})-F_c|_{base})]$ versus $\log(T_0)$ for each of the plurality of standard samples, where $t_{m2}$ represents a second time point in the amplification time interval.

25. The method of claim 24, wherein said step of determining which of the first and second relationships better satisfies the statistical criterion comprises the steps of:
   fitting the first set of points to a first line;
   fitting the second set of points to a second line; and
   determining which of the first and second lines provides a better statistical fit to its respective curve.

26. The method of claim 25, wherein said step of determining which of the first and second lines provides a better statistical fit comprises the steps of:
   determining a first T-value as the slope of the first line divided by a standard error in the slope of the first line; and
   determining a second T-value as the slope of the second line divided by a standard error in the slope of the second line.

27. An apparatus for determining a quantity of a nucleic acid sequence in a sample, comprising:
   means for measuring indicia of quantities of nucleic acid target and control sequences being amplified in a test sample, which contains an unknown starting quantity of the nucleic acid target sequence and a known starting quantity of the nucleic acid control sequence therein, and in a plurality of standard samples which each contain respective known starting quantities of the nucleic acid control and target sequences therein;
   means for determining an amplification ratio from the measured indicia of the amplified quantities of the nucleic acid control and target sequences in the standard samples; and
   means for determining a magnitude of the starting quantity of the nucleic acid target sequence in the test sample from the amplification ratio and the measured indicia of the amplified quantities of the nucleic acid control and target sequences in the test sample.

28. The apparatus of claim 27, wherein said measuring means comprises means for measuring first indicia of the amplified quantities of the nucleic acid control and target sequences in each of the standard samples during a first measurement time interval, and measuring second indicia of the amplified quantities of the nucleic acid control and target sequences in each of the standard samples during a second measurement time interval; and wherein said means for determining an amplification ratio comprises means for determining first and second amplification ratios from the first and second indicia, respectively.

29. The apparatus of claim 28, wherein said means for determining a magnitude comprises means for determining, relative to a statistical criterion, which of the first and second amplification ratios better satisfies the statistical criterion against the known starting quantities of the nucleic acid target sequence in the standard samples.

30. The apparatus of claim 27, wherein said measuring means comprises means for measuring control and target fluorescence intensities which are a function of the amplified quantities of the nucleic acid control and target sequences in a first standard sample containing equal starting quantities of the nucleic acid control and target sequences therein; and wherein said means for determining an amplification ratio comprises:
   means for determining control and target fluorescence relationships $(F_c(t))$ and $(F_T(t))$ as a function of time (t) for the first standard sample, from the measured control and target fluorescence intensities; and
   means for determining an amplification ratio (R*) based on the following relationship (where $C_0$ and $T_0$ represent the equal starting quantities of the nucleic acid control and target sequences in the first standard sample, respectively): $\log[(F_T(t)-F_T|_{base})/((F_c(t)-F_c|_{base}) R^*)] = \log T_0 - \log C_0$.

31. The apparatus of claim 27, wherein the plurality of standard samples comprise first and second standard samples which each contain equal starting quantities of the nucleic acid control and target sequences therein; wherein said measuring means comprises means for measuring first indicia of the amplified quantities of the nucleic acid control and target sequences in each of the standard samples and test sample during a first measurement time interval; and wherein said means for determining an amplification ratio comprises:
   means for determining a first amplification ratio from the measured first indicia of the amplified quantities of the nucleic acid control and target sequences in the first standard sample;
   means for determining a second amplification ratio from the measured first indicia of the amplified quantities of the nucleic acid control and target sequences in the second standard sample; and
   means for averaging the first and second amplification ratios to obtain a first average amplification ratio ($\overline{R}_1^*$).

32. The apparatus of claim 31, wherein said means for determining a magnitude comprises means for determining a magnitude of the starting quantity of the nucleic acid target sequence in the test sample from the first average amplification ratio and the measured indicia of the amplified quantities of the nucleic acid control and target sequences in the test sample.

33. An apparatus for determining a quantity of a nucleic acid sequence in a sample, comprising:
   means for measuring first and second indicia of quantities of nucleic acid target and control sequences being amplified in a test sample and a plurality of standard samples, at first and second measurement time intervals, respectively, the test sample containing an unknown starting quantity of the nucleic acid target sequence and a known starting quantity of the nucleic acid control sequence therein and the plurality of standard samples each containing respective known starting quantities of the nucleic acid control and target sequences therein;
   means for determining a first relationship between the first indicia and the known starting quantities of the nucleic acid target sequences in the standard samples;
   means for determining a second relationship between the second indicia and the known starting quantities of the nucleic acid target sequences in the standard samples;
   means for determining, relative to a statistical criterion, which of the first and second relationships better satisfies the statistical criterion against the known starting quantities of the nucleic acid target sequences in the standard samples; and
   means for determining a magnitude of the starting quantity of the nucleic acid target sequence in the test sample from the first or second relationship determined to better satisfy the statistical criterion.

34. A computer program product readable by a machine having means operatively coupled thereto for measuring indicia of quantities of nucleic acid target and control sequences being amplified in a test sample, which contains an unknown starting quantity of the nucleic acid target sequence and a known starting quantity of a nucleic acid control sequence therein, and in a plurality of standard samples which each contain respective known starting quantities of the nucleic acid control and target sequences therein, and tangibly embodying a program of instructions executable by the machine to perform the method steps of:

determining an amplification ratio from the measured indicia of the amplified quantities of the nucleic acid control and target sequences in the standard samples; and determining a magnitude of the starting quantity of the nucleic acid target sequence in the test sample from the amplification ratio and the measured indicia of the amplified quantities of the nucleic acid control and target sequences in the test sample.

35. The computer program product of claim 34, wherein the plurality of standard samples include first and second standard samples which each contain equal starting quantities of nucleic acid control and target sequences therein; and wherein said measuring means comprises means for measuring first indicia of the amplified quantities of the nucleic acid control and target sequences in each of the plurality of standard samples and test sample during a first measurement time interval.

36. The computer program product of claim 35, wherein said step of determining an amplification ratio comprises the steps of:

determining a first amplification ratio from the measured first indicia of the amplified quantities of the nucleic acid control and target sequences in the first standard sample;

determining a second amplification ratio from the measured first indicia of the amplified quantities of the nucleic acid control and target sequences in the second standard sample; and averaging the first and second amplification ratios to obtain a first average amplification ratio ($\overline{R}_1^*$).

37. The computer program product of claim 36, wherein the plurality of standard samples include a third standard sample having unequal starting quantities of the nucleic acid control and target sequences therein; wherein said measuring means comprises means for measuring control and target fluorescence intensities which are a function of the amplified quantities of the nucleic acid control and target sequences in the third standard sample, during the first measurement time interval; and wherein said step of determining a magnitude comprises the steps of:

determining control and target fluorescence relationships ($F_c(t)$) and ($F_T(t)$) as a function of time (t) for the third standard sample, from the measured control and target fluorescence intensities; and determining a relationship between ($F_T(t)$-$F_T|_{base}$)/(($F_c(t)$-$F_c|_{base}$)$\overline{R}_1^*$) and $T_0$, where $T_0$ represents the starting quantity of the nucleic acid target sequence in the third standard sample.

38. The computer program product of claim 37, wherein said step of determining a relationship comprises determining $\log [(F_T(t)-F_T|_{base})/((F_c(t)-F_c|_{base}) \overline{R}_1^*)]$ versus $\log (T_0)$.

39. The computer program product of claim 36, wherein said measuring means comprises means for measuring second indicia of the amplified quantities of the nucleic acid control and target sequences in each of the plurality of standard samples and test sample during a second measurement time interval; and wherein said step of determining an amplification ratio comprises the steps of:

determining a third amplification ratio from the measured second indicia of the amplified quantities of the nucleic acid control and target sequences in the first standard sample;

determining a fourth amplification ratio from the measured second indicia of the amplified quantities of the nucleic acid control and target sequences in the second standard sample; and averaging the third and fourth amplification ratios to obtain a second average amplification ratio ($\overline{R}_2^*$).

40. The computer program product of claim 39, wherein said step of determining a magnitude comprises the steps of:

determining, relative to a statistical criterion, which of the first and second average amplification ratios ($\overline{R}_1^*$) and ($\overline{R}_2^*$) better satisfies the statistical criterion against the known starting quantities of the nucleic acid target sequence in the first and second standard samples; and determining a magnitude of the starting quantity of the nucleic acid target sequence in the test sample from the first or second average amplification ratio determined to better satisfy the statistical criterion.

41. A computer program product readable by a machine having means operatively coupled thereto for measuring first and second indicia of quantities of nucleic acid target and control sequences being amplified in a test sample and a plurality of standard samples, at first and second measurement time intervals, respectively, the test sample containing an unknown starting quantity of the nucleic acid target sequence and a known starting quantity of a nucleic acid control sequence therein and the plurality of standard samples each containing respective known starting quantities of the nucleic acid control and target sequences therein, and tangibly embodying a program of instructions executable by the machine to perform the method steps of:

determining a first relationship between the first indicia and the known starting quantities of the nucleic acid target sequence in the standard samples;

determining a second relationship between the second indicia and the known starting quantities of the nucleic acid target sequence in the standard samples;

determining, relative to a statistical criterion, which of the first and second relationships better satisfies the statistical criterion against the known starting quantities of the nucleic acid target sequences in the standard samples; and determining a magnitude of the starting quantity of the nucleic acid target sequence in the test sample from the first or second relationship determined to better satisfy the statistical criterion.

42. The computer program product of claim 41, wherein said means for measuring first and second indicia comprises means for measuring first indicia as first control and target fluorescence intensities and second indicia as second control and target fluorescence intensities; wherein the method steps include the step of determining control and target fluorescence relationships ($F_c(t)$) and ($F_T(t)$) as a function of time (t), from the measured first and second indicia.

43. The computer program product of claim 42, wherein the plurality of standard samples have equal starting quantities of nucleic acid control sequence therein; wherein said step of determining a first relationship comprises determining a first set of points from $\log[(F_T(t_{m1})-F_T|_{base})/(F_c(t_{m1})-F_c|_{base})]$ versus $\log (T_0)$ for each of the plurality of standard samples, where $T_0$ represents the starting quantity of the nucleic acid target sequence in a respective standard sample and $t_{m1}$ represents a first time point in the amplification time interval; and wherein said step of determining a second relationship comprises determining a second set of points from $\log[(F_T(t_{m2})-F_T|_{base})/(F_c(t_{m2})-F_c|_{base})]$ versus $\log (T_0)$ for each of the plurality of standard samples, where $t_{m2}$ represents a second time point in the amplification time interval.

44. The computer program product of claim 43, wherein said step of determining which of the first and second relationships better satisfies the statistical criterion comprises the steps of:

fitting the first set of points to a first line;

fitting the second set of points to a second line; and determining which of the first and second lines provides a better statistical fit to its respective curve.

45. The computer program product of claim 44, wherein said step of determining which of the first and second lines provides a better statistical fit comprises the steps of:

determining a first T-value as the slope of the first line divided by a standard error in the slope of the first line; and determining a second T-value as the slope of the second line divided by a standard error in the slope of the second line.

* * * * *